(12) United States Patent
Chow et al.

(10) Patent No.: US 7,981,062 B2
(45) Date of Patent: Jul. 19, 2011

(54) MECHANICALLY ACTIVATED OBJECTS FOR TREATMENT OF DEGENERATIVE RETINAL DISEASE

(75) Inventors: Alan Y. Chow, Wheaton, IL (US); George Y. McLean, Palo Alto, CA (US); Vincent Y. Chow, Hanover Park, IL (US); Jay Cech, St. Charles, IL (US); Christopher M. Bonner, Menlo Park, CA (US); Vladimir Gelfandbein, Mountain View, CA (US)

(73) Assignee: IMI Intelligent Medical Implants AG, Zug (CH)

( * ) Notice: Subject to any disclaimer, the term of this patent is extended or adjusted under 35 U.S.C. 154(b) by 0 days.

(21) Appl. No.: 12/576,891

(22) Filed: Oct. 9, 2009

(65) Prior Publication Data
US 2010/0121231 A1    May 13, 2010

Related U.S. Application Data

(63) Continuation of application No. 10/822,437, filed on Apr. 12, 2004, now abandoned, which is a continuation-in-part of application No. 10/186,295, filed on Jun. 28, 2002, now abandoned, which is a continuation-in-part of application No. 10/056,793, filed on Jan. 23, 2002, now Pat. No. 7,031,776.

(60) Provisional application No. 60/301,877, filed on Jun. 29, 2001.

(51) Int. Cl.
*A61H 1/00* (2006.01)
(52) U.S. Cl. .......................................... 601/46; 600/54
(58) Field of Classification Search .................. 128/845, 128/846, 849–853; 600/54, 236; 601/46
See application file for complete search history.

(56) References Cited

U.S. PATENT DOCUMENTS

| | | | |
|---|---|---|---|
| 793,004 A | 6/1905 | May |
| 1,684,860 A | 9/1928 | Catlin |
| 2,525,381 A | 10/1950 | Tower |
| 2,721,316 A | 10/1955 | Shaw |
| 2,760,483 A | 8/1956 | Tassicker |
| 3,320,947 A | 5/1967 | Knoll |
| 3,594,823 A | 7/1971 | Collins |
| 3,628,193 A | 12/1971 | Collins |

(Continued)

FOREIGN PATENT DOCUMENTS

DE    19529371    2/1997

(Continued)

OTHER PUBLICATIONS

U.S. Appl. No. 60/301,877, filed Jun. 29, 2001, Chow, et al.

(Continued)

*Primary Examiner* — Michael A. Brown
(74) *Attorney, Agent, or Firm* — Workman Nydegger

(57) ABSTRACT

Mechanically activated objects or devices for use in treating degenerative retinal diseases are provided. Such devices apply mechanical forces to tissues of an eye to effectuate treatment and are configured for chronic implantation (thereby applying chronic stimulation/irritation) in or on the eye. The devices may be configured for contact with a retina of the eye, preferably positioned in a subretinal space. Various embodiments comprise a moving member configured for chronic contact with at least a portion of the eye, which moving member is activated by an actuator. In some embodiments, the actuator may be distally located relative to the moving member. Alternatively, the moving member may be supported by a body member that, optionally, also supports the actuator.

17 Claims, 8 Drawing Sheets

U.S. PATENT DOCUMENTS

| | | |
|---|---|---|
| 3,699,970 A | 10/1972 | Brindley et al. |
| 3,766,311 A | 10/1973 | Boll |
| 3,769,961 A | 11/1973 | Fatt et al. |
| 3,848,608 A | 11/1974 | Leonard |
| 3,893,444 A | 7/1975 | Fatt |
| 3,914,800 A | 10/1975 | Collins |
| 3,995,635 A | 12/1976 | Higuchi et al. |
| 3,995,659 A | 12/1976 | Fatt |
| 3,998,659 A | 12/1976 | Wakefield |
| 4,001,867 A | 1/1977 | Kravitz et al. |
| 4,018,218 A | 4/1977 | Carlson et al. |
| 4,089,329 A | 5/1978 | Couvillon, Jr. et al. |
| 4,211,474 A | 7/1980 | Le Goff |
| 4,251,887 A | 2/1981 | Anis |
| 4,271,841 A | 6/1981 | Friedman |
| 4,272,910 A | 6/1981 | Danz |
| 4,326,529 A | 4/1982 | Doss et al. |
| 4,484,922 A | 11/1984 | Rosenwald |
| 4,525,776 A | 6/1985 | Eldumiati et al. |
| 4,551,149 A | 11/1985 | Sciarra |
| 4,600,004 A | 7/1986 | Lopez et al. |
| 4,601,545 A | 7/1986 | Kern |
| 4,603,697 A | 8/1986 | Kamerling |
| 4,614,193 A | 9/1986 | Liss et al. |
| 4,628,933 A | 12/1986 | Michelson |
| 4,664,117 A | 5/1987 | Beck |
| 4,667,676 A | 5/1987 | Guinta |
| 4,679,572 A | 7/1987 | Baker, Jr. |
| 4,750,498 A | 6/1988 | Graham |
| 4,810,050 A | 3/1989 | Hooper |
| 4,832,202 A | 5/1989 | Newman et al. |
| 4,873,448 A | 10/1989 | Shirai |
| 4,874,237 A | 10/1989 | Cringle |
| 4,955,378 A | 9/1990 | Grasso |
| 4,978,842 A | 12/1990 | Hinton et al. |
| 4,979,508 A | 12/1990 | Beck |
| 4,989,605 A | 2/1991 | Rossen |
| 5,016,633 A | 5/1991 | Chow |
| 5,024,223 A | 6/1991 | Chow |
| 5,025,811 A | 6/1991 | Dobrogowski et al. |
| 5,070,860 A * | 12/1991 | Grounauer ............ 600/236 |
| 5,099,829 A | 3/1992 | Wu |
| 5,109,844 A | 5/1992 | de Juan Jr., et al. |
| 5,109,846 A | 5/1992 | Thomas |
| 5,130,528 A | 7/1992 | Phillips, Jr. |
| 5,130,776 A | 7/1992 | Popovic et al. |
| 5,147,284 A | 9/1992 | Fedorov et al. |
| 5,154,174 A | 10/1992 | Hawlina |
| 5,159,927 A | 11/1992 | Schmid |
| 5,174,304 A | 12/1992 | Latina et al. |
| 5,223,728 A | 6/1993 | Gempe |
| 5,256,882 A | 10/1993 | Miyasaka |
| 5,338,991 A | 8/1994 | Lu |
| 5,341,798 A * | 8/1994 | Grounauer ............ 600/236 |
| 5,351,309 A | 9/1994 | Lee et al. |
| 5,360,438 A | 11/1994 | Fisher |
| 5,397,350 A | 3/1995 | Chow et al. |
| 5,411,540 A | 5/1995 | Edell et al. |
| 5,441,040 A * | 8/1995 | Williams, Jr. ............ 600/236 |
| 5,476,494 A | 12/1995 | Edell et al. |
| 5,491,349 A | 2/1996 | Komoto et al. |
| 5,496,355 A | 3/1996 | Lipsky |
| 5,522,864 A | 6/1996 | Wallace et al. |
| 5,556,423 A | 9/1996 | Chow et al. |
| 5,578,040 A | 11/1996 | Smith |
| 5,618,261 A * | 4/1997 | Nevyas ............ 600/236 |
| 5,648,655 A | 7/1997 | Rostoker |
| 5,674,263 A | 10/1997 | Yamamoto et al. |
| 5,717,201 A | 2/1998 | Lin et al. |
| 5,782,894 A | 7/1998 | Israel |
| 5,837,995 A | 11/1998 | Chow et al. |
| 5,843,147 A | 12/1998 | Testerman et al. |
| 5,865,839 A | 2/1999 | Doorish |
| 5,895,414 A | 4/1999 | Sanchez-Zambrano |
| 5,895,415 A | 4/1999 | Chow et al. |
| 5,904,144 A | 5/1999 | Hammang et al. |
| 5,935,155 A | 8/1999 | Humayun et al. |
| 5,944,747 A | 8/1999 | Greenberg et al. |
| 6,006,756 A | 12/1999 | Shadduck |
| 6,007,477 A | 12/1999 | Demenezes |
| 6,032,062 A | 2/2000 | Nisch |
| 6,066,675 A | 5/2000 | Wen et al. |
| 6,083,251 A | 7/2000 | Shindo |
| 6,101,411 A | 8/2000 | Newsome |
| 6,154,671 A | 11/2000 | Parel et al. |
| 6,035,236 A1 | 5/2001 | Jarding et al. |
| 6,230,057 B1 | 5/2001 | Chow et al. |
| 6,264,971 B1 | 7/2001 | Darougar et al. |
| 6,275,735 B1 | 8/2001 | Jarding et al. |
| 6,282,449 B1 | 8/2001 | Kamerling et al. |
| 6,298,270 B1 | 10/2001 | Nisch et al. |
| 6,324,429 B1 | 11/2001 | Shire et al. |
| 6,347,250 B1 | 2/2002 | Nisch et al. |
| 6,389,317 B1 | 5/2002 | Chow et al. |
| 6,393,327 B1 | 5/2002 | Scribner |
| 6,423,001 B1 | 7/2002 | Abreu |
| 6,427,087 B1 | 7/2002 | Chow et al. |
| 6,458,157 B1 | 10/2002 | Suaning |
| 6,511,508 B1 | 1/2003 | Shahinpoor et al. |
| 6,549,808 B1 | 4/2003 | Gisel et al. |
| 6,647,297 B2 | 11/2003 | Scribner |
| 6,718,209 B2 | 4/2004 | Williamson et al. |
| 7,003,355 B1 | 2/2006 | Suaning et al. |
| 7,031,776 B2 | 4/2006 | Chow et al. |
| 2002/0038134 A1 | 3/2002 | Greenberg et al. |
| 2002/0095139 A1 | 7/2002 | Ok et al. |
| 2002/0147464 A1 | 10/2002 | Peyman |
| 2003/0028225 A1 | 2/2003 | Chow et al. |
| 2003/0139784 A1 | 7/2003 | Morimoto et al. |
| 2004/0106965 A1 | 6/2004 | Chow |
| 2005/0004625 A1 | 1/2005 | Chow |
| 2005/0033202 A1 | 2/2005 | Chow et al. |
| 2006/0142818 A1 | 6/2006 | Chow |

FOREIGN PATENT DOCUMENTS

| | | |
|---|---|---|
| EP | 0084621 | 11/1982 |
| EP | 0233789 | 8/1987 |
| EP | 0325201 | 7/1989 |
| EP | 0501904 | 9/1992 |
| EP | 1061874 | 12/2000 |
| EP | 1061996 | 12/2000 |
| GB | 2229543 | 9/1990 |
| JP | 8-154897 | 6/1996 |
| JP | 9-266954 | 10/1997 |
| JP | 2000-24122 | 1/2000 |
| RU | 2025114 | 12/1994 |
| RU | 2054909 | 2/1996 |
| RU | 2062080 | 6/1996 |
| RU | 2062128 | 6/1996 |
| RU | 2063199 | 7/1996 |
| RU | 2072815 | 2/1997 |
| RU | 2074681 | 3/1997 |
| RU | 2074682 | 3/1997 |
| RU | 2074684 | 3/1997 |
| RU | 2077291 | 4/1997 |
| RU | 2086216 | 8/1997 |
| RU | 2089144 | 9/1997 |
| RU | 2090167 | 9/1997 |
| RU | 2093118 | 10/1997 |
| RU | 2098009 | 12/1997 |
| RU | 2098056 | 12/1997 |
| RU | 2102046 | 1/1998 |
| RU | 2128485 | 4/1999 |
| RU | 2146909 | 3/2000 |
| RU | 2161019 | 12/2000 |
| RU | 2177766 | 1/2002 |
| RU | 2189800 | 9/2002 |
| SU | 554863 | 4/1977 |
| SU | 839529 | 6/1981 |
| SU | 939020 | 6/1982 |
| SU | 1044283 | 9/1983 |
| SU | 1139446 | 2/1985 |
| SU | 1386208 | 4/1988 |
| SU | 1395316 | 5/1988 |
| SU | 1409264 | 7/1988 |
| SU | 1757666 | 8/1992 |
| SU | 1766401 | 10/1992 |

| | | |
|---|---|---|
| SU | 1801021 | 3/1993 |
| SU | 1827222 | 7/1993 |
| SU | 1833730 | 8/1993 |
| SU | 1837858 | 8/1993 |
| SU | 1826174 | 11/1996 |
| WO | WO 81/01511 | 6/1981 |
| WO | WO 03/002190 | 1/2003 |

OTHER PUBLICATIONS

Abrams, Dr. Susan B., "Implanted photodiodes could restore lost vision", Biophotonics Research, 1997, 2 pages.
Acheson, A., P.A. Barker, R.F. Alderson, F.D. Miller, et al., "Detection of Brain-Derived Neurotrophic Factor-Like Activity in Fibroblasts and Schwann Cells: Inhibition by Antibodies to NGF", Neuron, vol. 7, 1991, pp. 265-75.
Ando, Haruhisa, et al. "Design Consideration and Performance of a New MOS Imaging Device", IEEE, 1985, 6 pages.
Armington, J.C., Brigell, M., "Effects of Stimulus Location and Pattern Upon the Visually Evoked Cortical Potential and the Electroretinogram," *Intern. J. Neuroscience*, vol. 14, 1981, pp. 169-178.
A.Y. Chow, G.A. Peyman, J. Pulido, "Safety and Feasibility of Subretinal Artificial Silicon Retina Retinal Prosthesis for the Treatment of Patients with Retinitis Pigmentosa", ARVO (The Association of Research in Vision and Ophthalmology), Abstract Issue of Annual Meeting, For Lauderdale, Florida, Apr. 29-May 4, 2001, Abstract 5042-11:11 (1 page and cover page), Published Mar. 15, 2001.
Baylor, D.A. Fuortes, M.G.F., "Electrical Responses of Single Cones in the Retina of the Turtle," J. Physiol, vol. 207, 1970, pp. 77-92.
Bergmann-Schaefer, "Lehrbuch der Experimentalphysik" (Textbook of Experimental Physics), vol. II, "*Electricity and Magnetism*"by Prof. Dr.-Ing. H. Gobrecht, 1971, 3 pp. plus translation.
Bobsch, M.D., Joseph M. and Grosser, Ph.D., Morton "Newer Repair at the AXOM Level: A Merger of Microsurgery and Microelectronics," VCH Publishers, Inc., 1967.
Boettner, E.A., Wolter, J.R., "Transmission of the Ocular Media," Investigative Ophthalmology, vol. 1, 1962, pp. 776-783.
Bosco, A., and Linden, R., "BDNF and NT-4 Differentially Modulate Neurite Outgrowth in Developing Retinal Ganglion Cells", J Neurosci Res. vol. 57, 1999, pp. 759-769.
Brady, G.S., Clauser, H.R., Materials Handbook, Thirteenth Edition, New York, McGraw-Hill, 1991, pp. 739-740.
Brindley, G.S., "The Site of Electrical Excitation of the Human Eye," J. Physiol, vol. 127, 1995, pp. 189-200.
Brindley, G.S., "Beats Produced by Simultaneous Stimulation of the Human Eye with Intermittent Light and Intermittent or Alternating Electric Current," J. Physiol., vol. 164, 1962, pp. 156-167.
Brown, M.G. et al., "Monolithically Integrated 1 × 12 Array of Planar InGaAs/InP Photodiodes," Journal of Lightwave Technology, vol. LT-4, No. 3, Mar. 1986, pp. 283-286.
Caleo, M., Lodovichi, C., and Maffei, L., "Effects of Nerve Growth Factor on Visual Cortical Plasticity Require Afferent Electrical Activity", Eur. J. Neurosci., vol. 11, 199, pp. 2979-84.
Carmignoto, G., Maffei, L., Candeo, P., Canella, R. and Comelli, C., "Effect of NGF on the Survival of Rat Retinal Ganglion Cells Following Optic Nerve Section", J. Neurosci., vol. 9, 1989, pp. 1263-1272.
Chapin, D.M., et al., "A New Silicon p-n. Junction Photocell for Converting Solar Radiation into Electrical Power," Letters to the Editor, Journal of Applied Physics, vol. 25, 1954, pp. 676-7.
Chow, A.Y., "Electrical Stimulation of the Rabbit Retina with Subretinal Electrodes and High Density Microphotodiode Array Implants," ARVO Abstracts, Invest. Ophthalmol. Vis. Sci. 199334 (Suppl), p. 835.
Chow, A.Y., Pardue, M.T., Chow, V.Y., Peyman, G.A., et al., "Implantation of Silicon Chip Microphotodiode Arrays into the Cat Subretinal Space", IEEE Trans. Neu. Syst. Rehabil. Eng., vol. 9, 2001, pp. 86-95.
Chow et al., "Safety and feasibility of subretinal artificial silicon retina™ retinal prosthesis for the treatment of patients with retinitis pigmentosa", ARVO Abstract Issue of Annual Meeting, Fort Lauderdale, Florida, Apr. 29-May 4, 2001, Abstract 5041-11:11, Published Mar. 15, 2001, 2 pages.

Chow, A.Y., and Chow, V.Y., "Subretinal Electrical Stimulation of the Rabbit Retina", Neurosci. Lett. vol. 225, 1997, pp. 13-16.
Chow, A.Y., and Peachey, N., "The Subretinal Microphotodiode Array Retinal Prosthesis II", Ophthal. Res., vol. 31, 1999, p. 246.
International Search Report for PCT/US02/20808 dated Mar. 21, 2003.
International Search Report for PCT/US02/20557 dated May 1, 2003.
Cui, Q., So, K.F., and Yip, H.K., "Major Biological Effects of Neurotrophic Factors on Retinal Ganglion Cells in Mammals", Biol. Sig. Recept., vol. 7, 1998, pp. 220-226.
Curcio, C.A., Sloan, K.R., Kalina, R.E., Hendrickson, A.E., "Human Photoreceptor Topography," J Comp. Neuro., vol. 292, 1990, pp. 497-523.
Dawson, W.W., Radtke, N. D., "The Electrical Stimulation of the Retina by Indwelling Electrodes," Invest. Ophthalmol. Visual Sci., vol. 16, 1997, pp. 249-252.
Dooley, D.M., Sharkey, J., Keller, W., and Kasprak, W., "Treatment of Demyelinating and Degenerative Diseases by Electro Stimulation of the Spinal Cord", Med. Prog. Technol., vol. 6, 1978, pp. 1-14.
Dowling, J.E., Ripps, H., Visual Adaptation in the Retina of the Skate, J Gen Physiol., vol. 56, 1970, pp. 491-520.
Eagle, R.C., Lucier, A.C., Bernardino, V.B., et al., "Retinal Pigment Epithelial Abnormalities in Fundus Flavimaculatus," Ophthalmol., vol. 87, 1980; pp. 1189-1200.
Evans, R.D., Foltz D., and Foltz, K., "Electrical Stimulation with Bone and Wound Healing", Clin. Podiatr. Med. Surg., vol. 18, 2001, pp. 79-95.
Fenwick, P.B.C., Stone, S.A., Bushman, J., Enderby, D., "Changes in the Pattern Reversal Visual Evoked Potential as a Function of Inspired Nitrous Oxide Concentration," Electroencephalogr. Clin. Neurophysiol., vol. 57, 1984, pp. 57178-57183.
John B. Flynn, et al. "Total Active Area Silicon Photodiode Array", 1964, 3 pages.
Frasson, M., Picaud, S., Leveillard, T., Simonutti, M., et al., "Glial Cell Line-Derived Neurotrophic Factor Induces Histologic and Functional Protection of Rod Photoreceptors in the rd/rd Mouse", Invest. Ophthalmol. Visual Sci., vol. 40, 1999, pp. 2724-2734.
Fujikado, Takashi, "Suprachoroidal-Transretinal Stimulation Effectively Elicits Localized Evoked Potential in RCS Rats", The first DOE International Symposium on Artificial Sight, Speaker Abstracts, May 2, 2003, p. 17.
Gibiliscos, S., and Sclater, N., Encyclopedia of Electronics, 2d Ed., 1990, pp. 640-645.
Graeme, J., "Position-Sensing Photodiode Amplifiers," Ch. 10, 12 pages.
Granit, R., Helme, T., "Changes in Retinal Excitability Due to Polarization and Some Observations on the Relation Between the Processes in Retina and Nerve," J. Neurophysiol., vol. 2, 1939, pp. 556-565.
Hagins, W.A., Penn, R.D., Yoshikami, S., "Dark Current and Photocurrent in Retinal Rods," J. Biophys, vol. 10, 1970, pp. 280-412.
Hergert, K., "Detectors: Expanded Photodetector Choices Pose Challenges for Designers", The Photonics and Design and Applications Handbook (1996).
Humayun, M.S., Propst, R.H., Hickinbotham, D., de Juan E., Jr., Dagnelie G., "Visual Sensations Produced by Electrical Stimulation of the Retinal Surface in Patients with End-Stage Retinitis Pigmentosa (RP)," ARVO Abstracts, Invest. Ophthalmol. Vis. Sci., vol. 34 Suppl, 1993, p. 835.
Humayun, M., Popst R., de Juan, E., et al., "Bipolar Surface Electrical Stimulation of the Vertebrate Retina, " Arch. Ophthalmol., vol. 112, 1994, pp. 110-116.
Kanda, H., "Suprachoroidal-Transretinal Stimulation (STS) Can Elicit Localized Evoked Responses From the Superior Colliculus in Normal and RCS Rats", ARVO Presentation Abstract, 2003, 1 page.
Kane, W.J., "Direct Current Electrical Bone Growth Stimulation for Spinal Fusion", Spine, vol. 13, 1988, pp. 363-365.
Kataoka, S., "An Attempt Towards an Artificial Retina: 3-D IC Technology for and Intelligent Image Sensor," Transducers '85: International Conference on Solid-State Sensors and Actuators 1985, pp. 440-442.

Klinke, R., Kral, A., Heid, S., Tillein, J., and Hartmann, R., "Recruitment of the Auditory Cortex in Congenitally Deaf Cats by Long-Term Cochlear Electrostimulation", Science, vol. 285, 1999, pp. 1729-1733.

Knighton, R.W., "An Electrically Evoked Slow Potential of the Frog's Retina. I. Properties of Response," J. Neurophysiol. vol. 38, 1975, pp. 185-197.

Koyama, S., Haruyama, T., Kobatake, E., and Aizawa, M., "Electrically Induced NGF Production by Astroglial Cells", Nature Biotechnol., vol. 15, 1997, pp. 164-166.

Lagey, C.L., Roelofs, J.M., Janssen, L.W.M., Breedijk, M., et al., "Electrical Stimulation of Bone Growth with Direct Current", Clin. Orthop., No. 204, 1986, pp. 303-312.

Lambiase, A., and Aloe, L., "Nerve Growth Factor Delays Retinal Degeneration in C3H Mice", Graefe's Arch. Clin. Exp. Ophthalmol., vol. 234, 1996, pp. 96-100.

Leake, P.A., Hradek, G.T., and Snyder, R.L., "Chronic Electrical Stimulation by a Cochlear Implant Promotes Survival of Spiral Ganglion Neurons after Neonatal Deafness", J. Comp. Neurol., vol. 412, 1999, pp. 543-562.

Leake, P.A., Hradek, G.T., Rescher, S.J., and Snyder, R.L., "Chronic Intracochlear Electrical Stimulation Induces Selective Survival of Spiral Ganglion Neuron in Neonatally Deafened Cats", Hear. Res., vol. 54, 1991, pp. 251-271.

Lin, H-C et al., "The Vertical Integration of Crystalline NMOS and Amorphous Orientational Edge Detector" IEEE Briefs, 1992, 3 pages.

Majji, Ajit, et al.: "Long Term Histological and Electrophysiological Results of an Inactive Epiretinal Electrode Array Implantation in Dogs", Investigative Ophthalmology & Visual Science, Aug. 1999, vol. 40, No. 9, pp. 2073-2081.

Margalit, et al.: "Bioadhesives for Intraocular Use", Retina, The Journal of Retinal and Vitreous Diseases, 2000, vol. 20, No. 5, pp. 469-477.

Melen, R.D., et al., "A Transparent Electrode CCD Image Sensor for a Reading Aid for the Blind," IEEE Journal of Solid-State Circuits, vol. SC-9, No. 2, Apr. 1974, pp. 41-48.

Miyoshi et al., "Inhibition of Neuronal Death of Retinal Ganglion Cell by Nerve Activation Using Electrical Stimulation", Vision Forum, 5th Annual Meeting, The Kitakyushu Science and Research Park Open Commemorative Project Assent: "Symposium of Visual Neuroscience and IT.", 4 pages.

Morimoto et al., "Electrical stimulation enhances the survival of axotomized retinal ganglion cells in vivo", Neuroreport, Feb. 11, 2002, vol. 13, No. 2, pp. 227-230.

Nakauchi, K., "Transretinal Electrical Stimulation by Intrascleral Multichannel Electrode in Rabbit Eyes Reviewing Code: 237 retinal prostheses—RE", ARVO Presentation Abstract, 2003, 1 page.

Narayanan, M.V., Rizzo, J.F., Edell, D., et al., "Development of a Silicon Retinal Implant: Cortical Evoked Potentials Following Focal Stimulation of the Rabbit Retina with Light and Electricity," ARVO Abstracts, Invest. Ophthalmol. Vis. Sci., vol. 35 (Suppl), 1994, p. 1380.

Neely, M.D., and Nicholls, J.G., "Electrical Activity, Growth Cone Motility and the Cytoskeleton", J. Exp. Biol. vol. 198, 1995, pp. 1433-1446.

Pagon, R.A., "Retinitis Pigmentosa," Survey Ophthalmol., vol. 33, 1988, pp. 137-177.

Paton, D., Goldberg, M.F., Management of Ocular Injuries, Philadelphia, W.B. Saunders Co., 1976, pp. 134-135.

Peachy, N. S., and Chow, A.Y., "Subretinal Implantation of Semiconductor-Based Photodiodes: Progress and Challenges", J. Rehabil. Res. Develop., vol. 36, No. 4, 1999, pp. 1-7.

The Penguin Dictionary of Electronics, Editor: Illingworth, V., Young, C., Market House Books Ltd., 1988, pp. 410-413.

Peyman, Gholam, MD, et al.: "Subretinal Semiconductor Microphotodiode Array", Ophthalmic Surgery and Lesers, Mar. 1998, vol. 29, No. 3, pp. 234-241.

Politis, M.J., Zanakis, M.F., and Albala, B.J., "Facilitated Regeneration in the Rat Peripheral Nervous System Using Applied Electric Fields", J. Trauma., vol. 28, 1988, pp. 1375-1381.

Politis, M.J., Zanakis, M.F., and Albala, B.J., "Mammalian Optic Nerve Regeneration Following the Application of Electric Fields", J. Trauma, 1988, vol. 28 pp. 1548-1552.

Politis, M.J., and Zanakis, M.F., "Short Term Efficacy of Applied Electric Fields in the Repair of the Damaged Rodent Spinal Cord: Behavioral and Morphological Results", Neurosurgery, vol. 23, 1988, pp. 582-588.

Politis, M.J., and Zanakis, M.F., "The Short-Term Effects of Delayed Application of Electric Fields in the Damaged Rodent Spinal Cord", Neurosurgery, vol. 25, 1989, pp. 71-75.

Politis, M.J., and Zanakis, M.F., "Treatment of the Damaged Rat Hippocampus with a Locally Applied Electric Field" Exp. Brain Res., vol. 71, 1988, pp. 223-226.

Potts, A.M., Inoue J., Buffum D., "The Electrically Evoked Response of the Visual System (EER)," Invest. Ophthalmol Vis Sci., 1968; 7:269-278.

Reh, T.A., McCabe, K., Kelley, M.W., and Bermingham-McDonogh, O., "Growth Factors in the Treatment of Degenerative Retinal Disorders", Ciba Found. Symp., vol. 196, 1996, pp. 120-131.

Robblee, L.S., Electrochemical Guidelines for Selection of Protocols and Electrode Materials for Neural Stimulation, Ch. 2, Renner Learning Resource Center (undated), pp. 25-66.

Rovamo, J., Virsu, V., "An Estimation and Application of the Human Cortical Magnification Factor," Exp Brain Res., vol. 37, 1979, pp. 495-510.

Rubin, M.L., Optics for Clinicains, Gainsville, TRIAD Scientific Publishers, 1974, pp. 119-123.

Shannon, R.V., "A Model of Safe Levels for Electrical Stimulation," IEEE Transactions Biomed. Eng., vol. 39, 1992, pp. 424-426.

Smith, J., "Creating a Bionic Eye", ABC News, Nov. 5, 1998, 3 pages.

Stone, J.L., Barlow, W.E., Humayun, M.S., de Juan, E., Jr., Milam, A.H., "Morphometric Analysis of Macular Photoreceptor and Ganglion Cells in Retinas with Retinitis Pigmentosa," Arch Ophthalmol., vol. 100, 1992, pp. 1634-1639.

Sze, S.M., "Physics of Semiconductor Devices", 2nd Ed., A Wiley-Interscience Publication, John Wiley & Sons, (undated).

Tasman, E. ed. Duane's Foundations of Clinical Ophthamology, vol. 3, Philadelphia, Lippincott, 1992; chapter 13:20-25, chapter 60: 1-112.

Terr, L.I., Linthicum, F.H., House, W.F., "Histopathologic Study of the Cochlear Nuclei After 10 Years of Electrical Stimulation of the Human Cochlea," Am. J. Otology., vol. 9, 1988, pp. 1-7.

Tomita, T., "Electrical Activity of Vertebrate Photoreceptor," Q. Rev. Biophys., vol. 3, 1970, pp. 179-222.

Wen, R. et al., "Injury-Induced Upregulation of bFGF and CNTF mRNAS in the Rat Retina", The Journal of Neuroscience, Nov. 1995, pp. 7377-7385.

Yokoyama et al., "Protection and retinal ganglion cells from ischemia-reperfusion injury by electrically applied Hsp27", Investigative Ophthalmology & Visual Science, Dec. 2001, vol. 42, No. 13, pp. 3283-3286.

Zrenner, E., et al., "The Development of Subretinal Microphotodiodes for Replacement of Degenerated Photoreceptors", Ophthalmic Res., 1997, pp. 269-280.

U.S. Appl. No. 10/056,793, Mail Date Sep. 15, 2004, Office Action.
U.S. Appl. No. 10/056,793, Mail Date Feb. 9, 2005, Office Action.
U.S. Appl. No. 10/056,793, Mail Date Aug. 25, 2005, Notice of Allowance.
U.S. Appl. No. 10/186,295, Mail Date Jul. 22, 2005, Office Action.
U.S. Appl. No. 10/186,295, Mail Date Oct. 21, 2005, Office Action.
U.S. Appl. No. 10/186,295, Mail Date Apr. 18, 2006, Office Action.
U.S. Appl. No. 10/186,295, Mail Date Sep. 25, 2006, Office Action.
U.S. Appl. No. 10/186,295, Mail Date Oct. 31, 2007, Office Action.
U.S. Appl. No. 10/186,295, Mail Date Jul. 8, 2008, Office Action.
U.S. Appl. No. 10/822,437, Mail Date Jan. 7, 2008, Office Action.
U.S. Appl. No. 10/822,437, Mail Date Jun. 11, 2008, Office Action.
U.S. Appl. No. 10/822,437, Mail Date Dec. 15, 2008, Office Action.
U.S. Appl. No. 10/822,437, Mail Date Jun. 18, 2009, Notice of Allowance.
U.S. Appl. No. 10/822,437, Mail Date Jul. 9, 2009, Notice of Allowance.
U.S. Appl. No. 10/606,117, Mail Date Apr. 26, 2006, Office Action.
U.S. Appl. No. 10/606,117, Mail Date Aug. 9, 2006, Office Action.

U.S. Appl. No. 10/606,117, Mail Date Jan. 16, 2007, Office Action.
U.S. Appl. No. 10/863,519 Mail Date Sep. 12, 2006, Office Action.
U.S. Appl. No. 10/863,519, Mail Date Nov. 22, 2006, Office Action.
U.S. Appl. No. 11/301,352, Mail Date Oct. 30, 2008, Office Action.
U.S. Appl. No. 11/301,352, Mail Date Feb. 24, 2009, Office Action.
U.S. Appl. No. 11/301352, Mail Date Jun. 9, 2009, Office Action.

* cited by examiner

MECHANICALLY ACTIVATED OBJECTS FOR TREATMENT OF DEGENERATIVE RETINAL DISEASE

CROSS-REFERENCE TO RELATED APPLICATIONS

This application is a continuation of U.S. application Ser. No. 10/822,437, filed Apr. 12, 2004, which is a continuation-in-part of U.S. application Ser. No. 10/186,295, filed Jun. 28, 2002, now abandoned, which is a continuation-in-part of U.S. application Ser. No. 10/056,793, filed Jan. 23, 2002, now U.S. Pat. No. 7,031,776, granted Apr. 18, 2006, which claims the benefit of Provisional Application Ser. No. 60/301,877, filed Jun. 29, 2001, which prior applications are hereby incorporated by reference in their entirety.

FIELD OF THE INVENTION

The present invention is directed generally to improving biological cell function and more specifically to improving retinal cell visual function in damaged and/or degenerated retinas and also to protecting retinal cells from degeneration.

BACKGROUND

Certain biological chemical compounds such as nerve growth factors (NGF), neurotrophins, brain-derived neurotrophic factors (BDNF), fibroblastic growth factor (FGF), glial cell line-derived neurotrophic factors (GDNF), and numerous other similar biological chemical compounds, all collectively known as survival-type factors can slow down the process of cellular degeneration in a number of biological degenerative diseases, specifically in retinal degenerative diseases and also promote cellular growth in other situations.

In studies, the application of survival-type factors was found to promote and maintain certain retinal cellular functions. For example, brain-derived neurotrophic factor (BDNF), neurotrophin-4 (NT-4), neurotrophin-5 (NT-5), fibroblastic growth factor (FGF) and glial cell line-derived neurotrophic factor (GDNF) have been shown to enhanced neurite outgrowth of retinal ganglion cells and to increase their survival in cell culture. GDNF has been shown to preserve rod photoreceptors in the rd/rd mouse, an animal model of retinal degeneration. Nerve growth factor (NGF) injected into the intra-ocular area of the C3H mouse, also a model of retinal degeneration, results in a significant increase of surviving photoreceptor cells compared to controls (Bosco and Linden, 1999; Caleo et al., 1999; Carmignoto et al., 1989; Cui et al., 1998; Frasson et al., 1999; Lambiase and Aloe, 1996; Reh et al., 1996).

However, while many prostheses are known that attempt to restore vision by using photoactive properties of semiconductors designed to provide sufficient electrical stimulation of retinal cells to induce a perceptual response, few devices or treatments are available that can slow, stop or reverse retinal degeneration.

SUMMARY

The present invention provides mechanically activated objects or devices for use in treating degenerative retinal diseases. In particular, devices in accordance with the present invention provide stimulus/irritation to tissues of an eye through active mechanical forces to effectuate treatment of a degenerative retinal disease. It is hypothesized that such mechanical forces, when applied to tissues of the eye, stimulate the production of beneficial materials such as survival-type factors, particularly neurotrophic growth factors, in response to the irritation or trauma of the eye tissues.

In one embodiment, devices in accordance with the present invention are configured for chronic implantation (thereby applying chronic stimulation/irritation) in or on an eye. More particularly, such devices may be configured for contact with a retina of the eye, preferably positioned in a subretinal space. Various embodiments of the present invention comprise a moving member configured for chronic contact with at least a portion of the eye, which moving member is activated by an actuator. In some embodiments, the actuator may be distally located relative to the moving member. Alternatively, the moving member may be supported by a body member that, optionally, also supports the actuator. Regardless, when activated by the actuator, the moving member stimulates or irritates the eye by causing displacement of at least a portion of the eye to thereby effectuate treatment.

DETAILED DESCRIPTION OF THE PRESENTLY PREFERRED EMBODIMENTS

Figure 1:
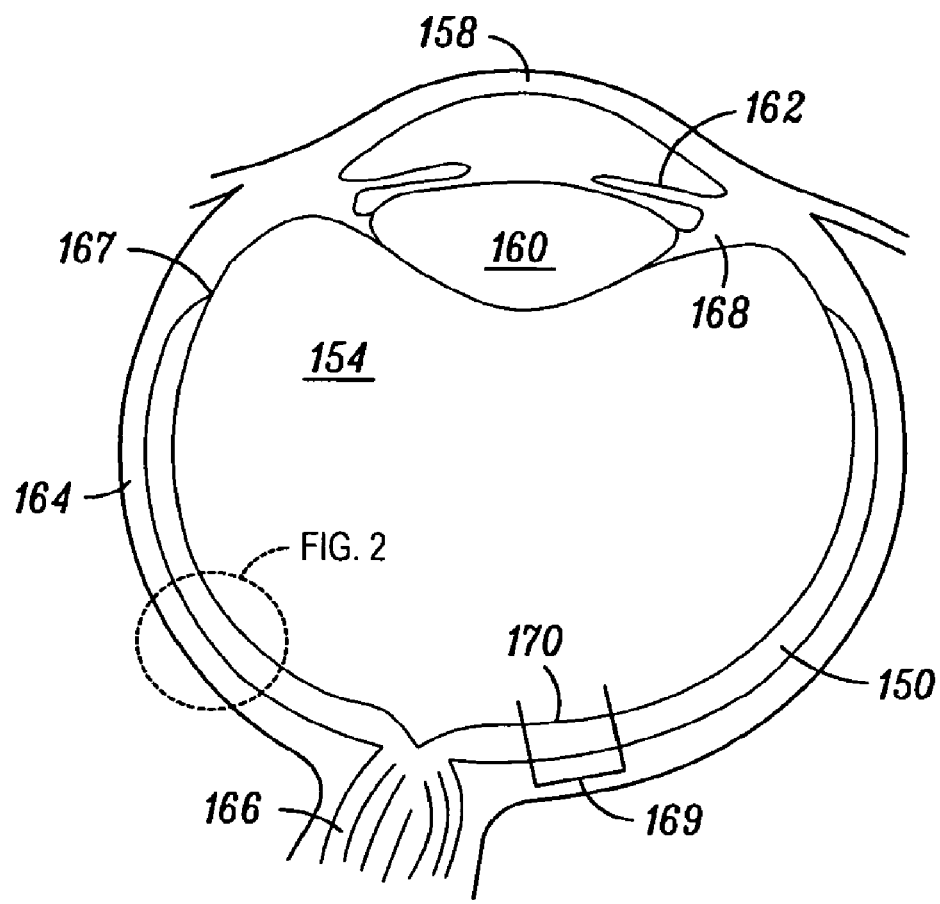
FIG. 1 presents a top cross-section of a human eye.

Many human retinal diseases cause vision loss by partial to complete destruction of the vascular layers of the eye that include the choroid and choriocapillaris, both of which nourish the outer anatomical retina and a portion of the inner anatomical retina of the eye. A number of other retinal diseases cause vision loss due to partial to complete degeneration of one or both of the two anatomical retinal layers directly, due to inherent abnormalities of these layers. The components of the retinal layers include Bruch's membrane and retinal pigment epithelium which comprise the "outer anatomical retinal layer", and the photoreceptor, outer nuclear, outer plexiform, inner nuclear, inner plexiform, amacrine cell, ganglion cell and nerve fiber layers which comprise the "inner anatomical retinal layer", also known as the "neuroretina". The outer portion of the neuroretina is comprised of the photoreceptor and bipolar cell layers and is also known as the "outer retina" which is to be distinguished from the "outer anatomical retinal layer" as defined above.

Loss of function of the outer retina is commonly the result of dysfunction of the outer anatomical retinal layer that provides nourishment to the outer retina and/or to direct defects of the outer retina itself. The final common result, however, is dysfunction of the outer retina that contains the light sensing cells, the photoreceptors. Some of these "outer retina" diseases include age-related macula degeneration, retinitis pigmentosa, choroidal disease, long-term retinal detachment, diabetic retinopathies, Stargardt's disease, choroideremia, Best's disease, and rupture of the choroid. The inner portion of the neuroretina, however, often remains functionally and anatomically quite intact and may be activated by the appropriate stimuli.

Although prosthetic electrical devices designed to replace damaged or missing retinal cells have been used to treat vision loss caused by outer retinal degeneration, physical stimulation to improve large areas of retinal cell visual function is novel. As a non-limiting explanation, the promotion of improved retinal cell visual function by physical stimulation may be explained by the stimulation of production and release of growth factors (GFs); more specifically, neurotrophic-type growth factors (NTGFs), by the stimulated retinas in response to the wounding or trauma inflicted by the physical stimulation. The synthesis and/or secretion of neurotrophic factors would then improve retinal cell function and survival in conditions where these activities would be lost.

Animal and human studies have been used to show that electrical stimulation may be used to improve the general inherent visual function of damaged retinal cells in direct contact with and surrounding an implanted electrical artificial silicon retina prosthesis (Chow et al., 2002). The mechanism of action may be related to the upregulation and production of endogenous survival-type factors by the retina due to an electrical effect on cellular membranes which may include a direct irritant effect of the electric current.

An irritant effect is also produced by the physical effect that includes a mechanical foreign-body effect, of an implant placed into or in contact with the retina. Such an irritant effect is akin to a mild damage effect on the retina which is known to upregulate the production of survival-type factors. For example, an incision into the retina, called a retinotomy, is known to upregulate, albeit temporarily, certain survival-type factors that also temporarily slow down retina degeneration in a rat model of retinal degeneration (Peng et al., 1997). A non-electrical foreign body that is inert or almost inert is therefore capable of producing a chronic irritant effect that chronically upregulates endogenous survival factors in the retina and to produce a long-term slowdown or prevention of a retinal degenerative process.

A system and method are disclosed of placing a non-electrical physical and/or mechanical foreign body into or in contact with the retina to irritate and therefore chronically stimulate the upregulation of survival-type factors to slow down and/or prevent retinal degeneration. The subject matter of this application also includes the devices used to produce the said chronic irritation of the retina. Such non-electrical chronic irritant devices theoretically may have the ability to slow down the degeneration in other organ systems such as the central nervous system.

The present invention discloses both devices and novel methods to non-electrically irritate and/or stimulate the retina by physical and/or mechanical stimulation/irritation to improve large areas of retinal visual function and to protect the retina from degeneration.

Definitions

Subject/Patient

A subject (patient) may be a human being or a non-human animal, but is preferably a human. Usually the individual has suffered some type of retinal damage and/or degeneration that results in some degree of visual loss and/or has a condition that will result in retinal damage and/or degeneration. A healthy subject does not have a condition that will result in retinal damage and/or degeneration and/or has not suffered retinal damage and/or degeneration.

Improving Visual Function

Improving visual function refers to improving a targeted function of the eye, selected by the artisan, and includes improving any to all of the following capabilities of the eye, retina and visual system: perception of brightness in the presence of light, perception of darkness in the absence of light, perceptions of contrast, color, shape, resolution, movement and visual field size.

Primary visual degradation means loss of visual function due to malfunction of, damaged to, or degeneration of structures found in the eye. Secondary visual degradation means loss of visual function due to secondary damage, typically from lack of use of the vision-associated portions of the brain. Improving visual function means to improve the visual function of primary visual degradation, secondary visual degradation or both.

Eye/Eyeball

The eye (or eyeball) has the usual definition in the art. Eye includes all interior and exterior surfaces, components, contents and cavities of the eye. The eye does not include the eyelid.

The retina of the eye can be divided into sectors as is commonly accepted in the art. Such sectors are described by the use of the terms temporal, nasal, superior, inferior, by clock hour designation, and by the number of degrees away from the macula. For example, the temporal sector of the retina is the retina temporal to a perpendicular plane cutting through retina from the 12 o'clock to the 6 o'clock positions and through the macula. In another example, the superior sector is the retina superior to a perpendicular plane cutting through the 9 o'clock to 3 o'clock positions and through the macula. In a further example, the superior-temporal sector is the intersection of these two sectors, a pie-shaped area delineated from the 9 o'clock position of the peripheral retina to the macula and then clockwise to the 12 o'clock position. More specific locations of the retina can be designated by degrees away from the macula and clock hour location: for example, 20 degrees away from the macula at the 3 o'clock (nasal) position. The number of degrees away from the macula is in visual axes degrees. These axes all intersect through the lens of the eye.

The visual field sectors correspond oppositely to the retinal sectors as is commonly understood in the art. For example, the superior-temporal sector of the retina corresponds to the inferior-nasal portion of the visual field.

Peripheral

To be peripheral to an object, device or other landmark includes all surrounding parts, but not the object, device or landmark, i.e., the object, device or landmark, together with the peripheral portion, constitutes the whole.

Light

Light refers not only to the electromagnetic spectrum that humans can readily perceive visually (approximately 400 nm to 750 nm), but also includes ultraviolet light (<400 nm in wavelength) as well as infrared light (>750 nm in wavelength).

Indications

The invention can be used to improve visual function in subjects in which the retina is damaged by disease, degeneration, condition, or trauma and/or to slow down or stop the progression of damage by disease, degeneration, condition or trauma. Common diseases, conditions, degeneration or trauma that are particularly amenable to this treatment include age-related macula degeneration, retinitis pigmentosa, Leber's congenital amaurosis, Stargardt's disease, Best's disease, diabetic retinopathy, long-term retinal detachment, and choroidal damage.

Eye Structure

Referring to the drawings, FIG. 1 illustrates a section through the eyeball. The neuroretina 150 comprises multiple layers of cells and structures (see FIG. 2). The photoreceptor components of the retina are situated within the neuroretina which covers the internal posterior cavity of the eye, terminating anteriorly at the ora serrata 167. The ciliary body 168 and the iris 162 are covered by extensions of the retina, lacking photoreceptor components. The outermost layers of the eye consist of the sclera 164 and cornea 158. The sclera is pierced by the emerging optic nerve 166. The lens 160 and vitreous cavity 154 are also indicated. The macula 169 of the retina is typically a 3 mm by 5 mm oval region, at the center of which is the fovea 170.

Figure 2:
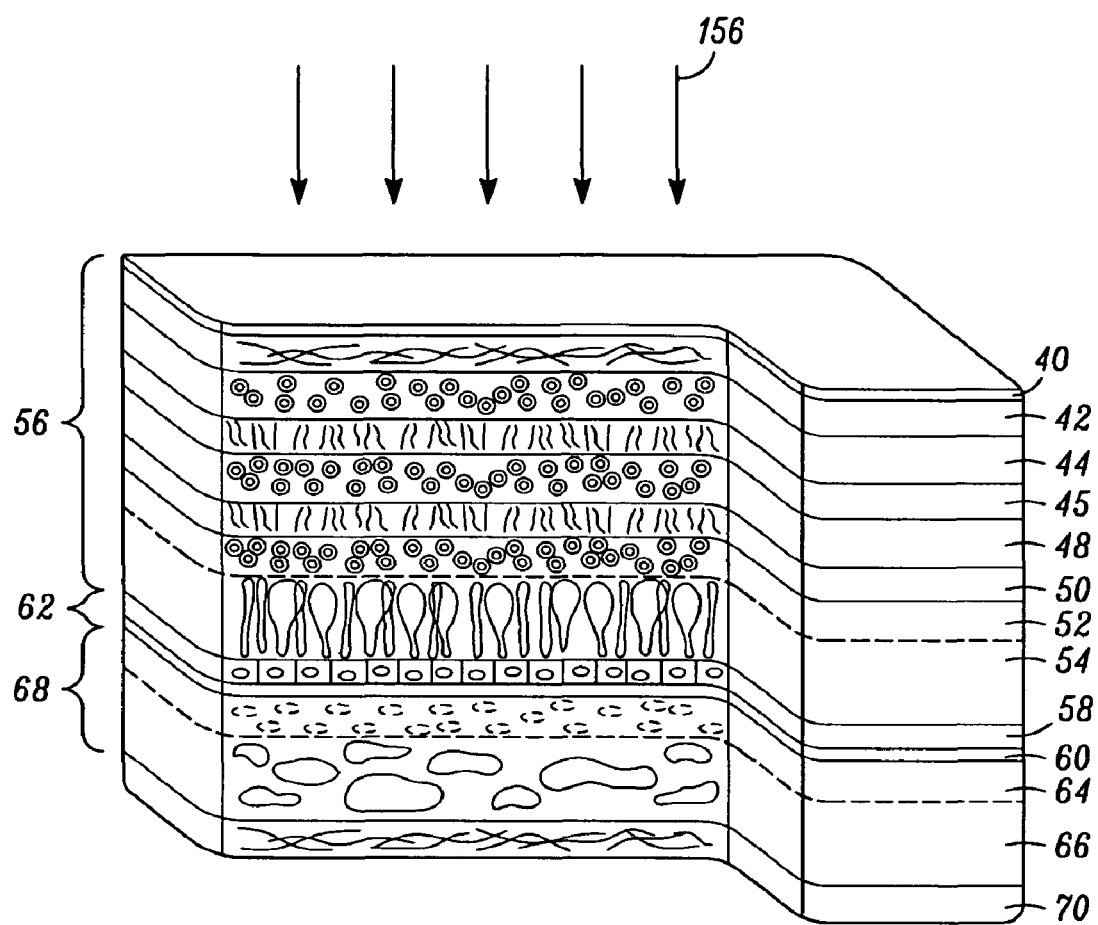
FIG. 2 presents a cross-section through the human eye that includes the layers of the outer and inner anatomical retina, as indicated by the inset of FIG. 1.

The layers of the eye at the posterior pole from inside to outside are shown in FIG. 2: internal limiting membrane 40, nerve fiber layer 42, ganglion and amacrine cell layer 44, inner plexiform 46, inner nuclear/bipolar cell layer 48, outer plexiform 50, outer nuclear layer 52, and photoreceptor layer 54, all of which constitute the anatomical inner retinal layer, also known as the neuroretina 56. The retinal pigment epithelium 58, and Bruch's membrane 60 constitute the outer retinal layer 62. The choriocapillaris 64, and choroid 66 comprise the choroidal vasculature 68. The outer coat of the eye is the sclera 70. Light 156 enters the retina as shown. As known in the art, a subretinal space is defined as the potential space existing between the outer anatomical retinal layer and the neuroretina.

Devices and Methods to Provide Physical Stimulation

Any object that can provide a chronic or prolonged physical stimulation or irritation to the eye can be used as a source of physical stimulation. These devices may include, but are not limited to, electrically inert objects, mechanically or electrically activated objects, and chemical or biological agents.

The physical stimulation may be provided by any object that can remain in physical contact with and/or irritate cells, such as retinal cells of an eye, for an extended period of time. The extended period of time may be years, such as would be the case with a device that would be implanted in the eye and persist indefinitely in the eye unless it was purposefully extracted. Alternatively, the extended period of time may be a limited time, for example one year, after which the implanted device or agent would biodegrade or otherwise be absorbed.

In one preferred embodiment, the source of physical stimulation is at least one device or object that is electrically inactive such that it is neither photoactive, a source of electrical stimulation, nor in electrical communication with a source of electrical stimulation. The device may be constructed from silicon, metal, plastic, ceramic, glass, wood, sand or any of a number of materials. For example, an object of any shape or depth may be used. These shapes may include, but not be limited to, to geometric shapes, such as straight lines, circles, squares, rectangles, and triangles as well as three-dimensional shapes, such as balls, cubes, cylinders, or cones.

Figure 3:
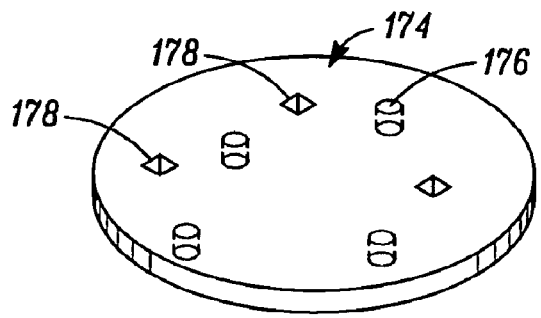
FIG. 3 illustrates one preferred shape of an implantable device.
Figure 4:
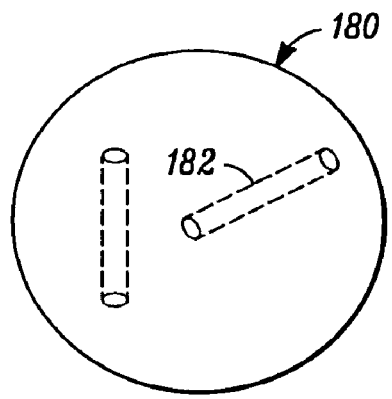
FIG. 4 illustrates a first alternative shape of the implantable device of FIG. 3.
Figure 5:
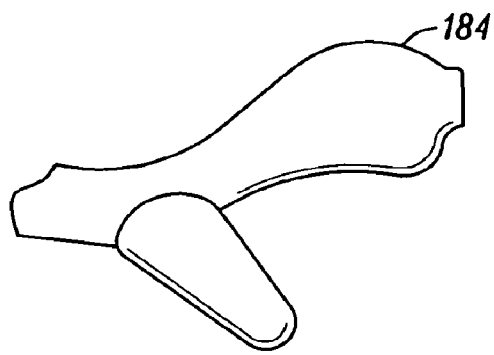
FIG. 5 illustrates a second alternative shape of the implantable device of FIG. 3.

Referring to FIGS. 3-5, several suitable shapes of implantable devices are shown. The device may be a disk-shaped object 174 with or without fenestrations 176, as shown in FIG. 3. In order to increase the surface area available to physically contact cells in the eye, the object 174 may be constructed to include various shape protrusions 178. The object 180 shown in FIG. 4 illustrates a spherical shape. Again, fenestrations 182 may be incorporated in the object to allow nutrients to pass through. Irregularly-shaped objects 184, such as illustrated in FIG. 5, may be also be used. While the devices may be of various different dimensions, one preferred size range is greater than approximately 1 micron and less than approximately 20 mm in linear dimensions, and more preferably greater than approximately 0.5 mm and less than approximately 5 mm in linear dimensions. Substrates for such objects include, without limitation, bio-absorbable polymers, silicon, plastics and other metals, and biomaterials. These devices can be implanted in any of the regions of an eye as discussed below. Many materials, shapes, sizes and devices may be used as long as they interact with cells in the eye to physically stimulate these cells. Also, in yet other embodiments, one or more electrically inert devices may be implanted in the eye in combination with one or more devices intended to supply electrical stimulation to the eye.

Figure 6:
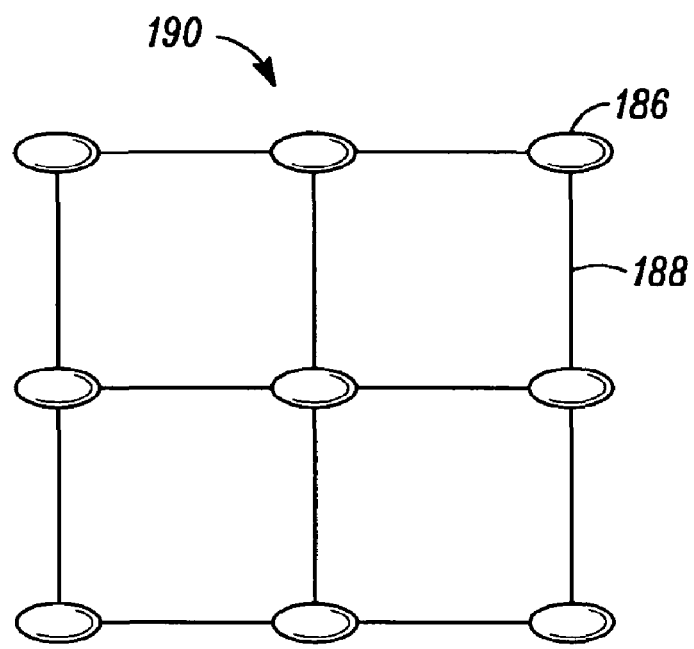
FIG. 6 is a two dimensional array of implantable devices.
Figure 7:
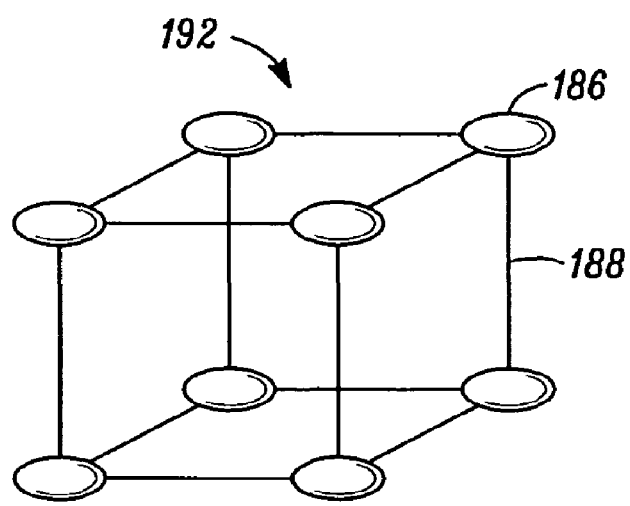
FIG. 7 is a three dimensional array of implantable devices.

In yet other embodiments, the device may be an interconnected array of implantable elements. For example, FIG. 6 shows a two dimensional array 190 of implantable objects 186 interconnected by a flexible biocompatible mesh 188. Each of the objects 186 may be of the same or different shape and maintains its physical connection with one or more of the other objects while in the eye via the mesh 188. Alternatively, as shown in FIG. 7, the array may be a three dimensional array 192 of implantable objects 186 interconnected by a flexible mesh 188.

Other means to provide physical stimulation includes implanting devices that deliver an irritant. For example, oils, detergents, bile salts, etc. may be applied in small quantities that are yet sufficient to physically stimulate the cells. Preferably, the irritant is packaged, such as in a capsule, so that the irritant is slowly released over time, and so that the "packaging" is ultimately absorbed by the body. Examples of biodegradable substances include biodegradable polymers. Biodegradable polymers decompose when placed inside an organism and thus eliminate the need to remove the implant after the bioactive agent has been released, since the polymer will gradually break down and may be metabolized or excreted from the body. The decomposition of a biodegradable polymer can be observed as a decline in the molecular weight of the polymer over time. Polymer molecular weights can be determined by a variety of methods including size exclusion chromatography (SEC), and are generally expressed as weight averages or number averages. A polymer is biodegradable if, when in phosphate buffered saline (PBS) of pH 7.4 and a temperature of 37° C., its weight-average molecular weight is reduced by at least 25% over a period of 6 months as measured by SEC.

Polymers which could be useful as "packaging" capsules include, but are not limited to, polyesters, such as poly(caprolactone), poly(glycolic acid), poly(lactic acid), poly(hydroxybutyrate); copolymers of caprolactone, glycolic acid, lactic acid, and hydroxybutyrate; polyanhydrides, such as poly(adipic anhydride); poly(para-dioxanone); poly(malic acid); polyamines; polyurethanes; polyesteramides; polyorthoesters; polyacetals; polyketals; polycarbonates; polyorthocarbonates; polyphosphazenes; poly(amino acids); chitin; chitosan; and copolymers and mixtures thereof.

Chemical or biological agents, including growth factors, can also be introduced into the eye to provide a prolonged stimulation to enhance rescue and retina functional improvement. This additional step is attractive because some factors, especially neurotrophic-type growth factors, may improve retinal function and provide limited neuronal rescue in eyes with retinal degeneration and dysfunction. These growth factors include, but are not limited to, glial cell line-derived neurotrophic factor (GDNF), nerve growth factor (NGF), brain derived neurotrophic growth factor (BDNGF), neurotropin-3 (NT-3), neurotropin-4 (NT-4), neurotropin-5 (NT-5), ciliary neurotropic factor (CNTF) and fibroblastic growth factor (FGF). These growth factors can be delivered to the eye by coating the device with growth factor(s) before implantation, by injection of the growth factor(s) into the locations of the subretinal space, vitreous cavity, subconjunctival space, subscleral space, and/or the anterior chamber either singly or in combination with each other, as a single dose or as multiple repeat doses before, during and/or after implantation of the device(s).

Location of Stimuli

The chronic physical stimulation provided by at least one device may be provided subretinally, epiretinally, subsclerally (between the sclera and choroid; also referred to as suprachoroidally), subchoroidally (between the choroid and Bruch's membrane), on the scleral surface, on or under the conjuctival surface and/or from or within any structure of the eye. Other means of providing physical simulation to the retina and eye may include devices that deliver chronic stimulation from the underside of the eyelid(s). Preferably, physical stimulation is from the subretinal space which is an area that is in close proximity to the damaged retinal cells.

Therefore, in one embodiment, the chronically irritating/stimulating agent can be inserted in a way that it is placed in direct contact with the damaged retinal cells. In another embodiment, the chronically irritating/stimulating agent can be placed adjacent to, but not in direct contact with, the damaged retinal cells. In response to the prolonged trauma inflicted by the irritant, healthy retinal cells may be chronically stimulated to produce and release growth factors, such as neurotrophic growth factors, to help enhance retinal cell function.

Implantation Sites and Surgical Methods

In one embodiment, the physical stimulation is preferably in the subretinal space in the periphery and/or mid-periphery of the eye, outside of the macula. For devices that are implanted, more than one device may be implanted, if needed, in an eye to stimulate a larger area of the retina, and multiple devices can be implanted in paracentral locations such as one in each of the four paracentral quadrants, approximately, but not limited to, 5 to 80 degrees peripheral to the macula. In other embodiments, one or more devices may be implanted in the macular region of the eye. In one embodiment the implants may be placed in the subretinal space in the mid-periphery approximately 20 degrees away from the macula, using one device or up to approximately four devices evenly spaced on a perimeter in the midperiphery. Cells to stimulate include the remaining cells of the inner retina.

In yet another embodiment, an implantable device is designed to be implanted onto the epiretinal surface (i.e. on the nerve fiber layer side) of the retina. It is retained in position by retinal tacks, biocompatible glues, or other means. In the case of electrical implantable devices, subconjunctival/scleral placement of the device results in less efficient electrical stimulation of the retina compared to a subretinally or epiretinally placed device, but the extraocular location of the device decreases the surgical risk to a patient since intraocular surgery would not be required for its implantation. The subconjunctival/scleral placement of a device also allows a stable device position to be achieved without fixating devices or glues (i.e., the device is held in place between the conjunctiva and sclera).

Surgical methods are well known in the art (Peyman et al., 2000). Descriptions of specific surgeries for implantation of electrical stimulation devices, which are also applicable to other physical stimulating devices, have been extensively described (Chow, U.S. Pat. No. 5,024,223, 1991; Chow and Chow, U.S. Pat. No. 5,397,350, 1995; Chow and Chow, U.S. Pat. No. 5,556,423, 1996; Chow and Chow, 1997; Chow et al., 2001; Chow and Peachey, 1999; Chow and Chow, U.S. Pat. No. 5,895,415, 1999; Chow and Chow, U.S. Pat. No. 6,230,057 B1, 2001).

In another embodiment, electrically inert objects, chemical, and/or biological agents can be inserted into an eye in several ways. Chemical and biological agents, such as growth factors, can be delivered to the eye by coating a substrate with these factor(s) before implantation and/or by injecting these factor(s) into the locations of the subretinal space, vitreous cavity, subconjunctival space, subscleral/suprachoroidal space, subchoroidal space and/or the anterior chamber either singly or in combination with each other, as a single dose or as multiple repeat doses independent of, before, during and/or after implantation of the coated substrate or other electrical stimulating device. Electrically inert object(s) can be delivered to the eye by placing it directly into the subretinal space, vitreous cavity, subconjunctival space, subscleral space, and/or the anterior chamber through implantation or injection performed as previously described for the retinal implantable devices.

Further embodiments in accordance with the present invention, particularly mechanically activated embodiments, are further illustrated in FIGS. 8-16. As used herein, mechanically activated embodiments are characterized by the use of mechanical action or forces to stimulate or irritate cells of the eye, as opposed to physical embodiments which, more generally, refer to the material presence of an object or device to effectuate stimulation/irritation and, hence, treatment of the eye. In general, each of the devices described below are dimensioned to fit on or within the eye, typically on the order of a few millimeters in length, although sub-millimeter devices or devices greater than around 10 millimeters may be possible. Additionally, the thicknesses of such devices, particularly where intended for subretinal implantation, are substantially smaller than the lengths, typically on the order of tens or hundreds of microns although, once again, larger or smaller thicknesses may be possible as a matter of design.

Figure 8:
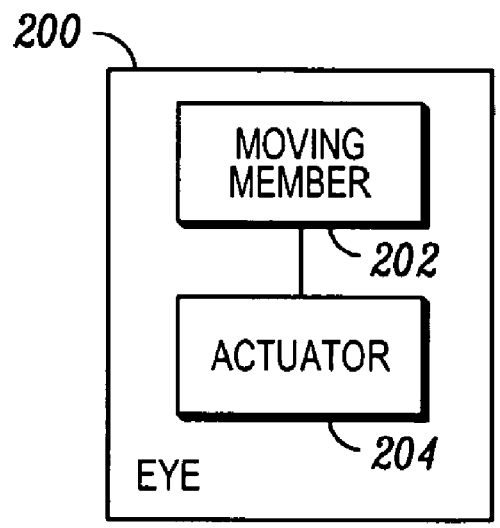
FIG. 8 is a schematic illustration of a mechanically activated object in accordance with one embodiment of the present invention.

A first schema of mechanically activated embodiments is illustrated in FIG. 8 wherein at least one moving member 202 is acted upon by an actuator 204, both of which are implanted on or within an eye 200. The moving member 202 is configured to contact at least a portion of the eye, including any of the various structures of the eye, preferably a retina of the eye. Furthermore, although preferably configured for implantation in the subretinal space, the moving member 202 may be equally configured for implantation in virtually any location of the eye, e.g., epiretinally, subchoroidally, subsclerally/suprachoroidally, sclerally, on the conjunctiva, etc. As used herein, an element is configured for a particular application, in part, through the choice of dimensions, materials and/or shape suitable for the particular application. Regardless of its location when implanted, the moving member 202, when acted upon by the actuator 204, imparts displaces the tissues of the eye with which it is in contact thereby stimulating the eye. As noted above, experimental studies suggest that such stimulation or irritation may induce a beneficial upregulation of endogenous survival-type factors.

Figure 9:
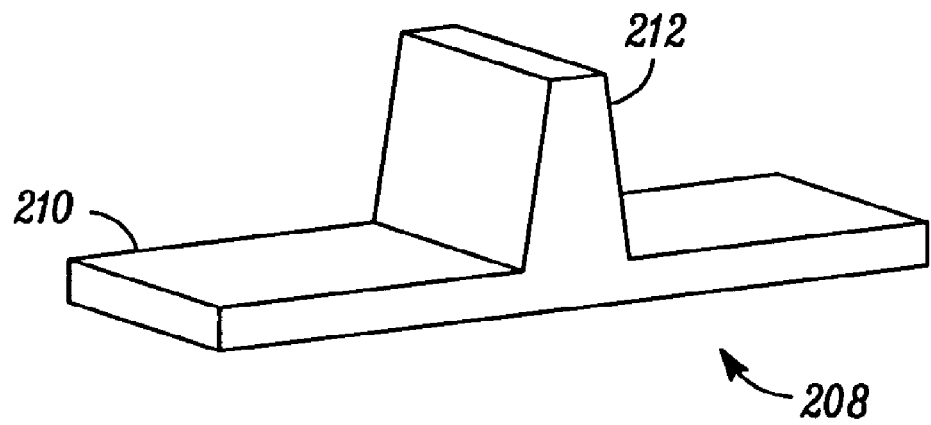
FIG. 9 is a perspective view of a first exemplary device in accordance with the schema of FIG. 8.

A first exemplary device 208 in accordance with the schema of FIG. 8 is illustrated in FIG. 9. In particular, the device 208 comprises a moving member 210 that is generally planar and fabricated from biocompatible, biodurable materials such as glass, polyimide, PDMA, parylene C, silicone, silicon, silicon dioxide, diamond-like materials, metals including titanium, iridium, stainless steel, gold, aluminum, various oxides thereof, etc. As know in the art, a combination of materials may be used to meet different design criteria, e.g., a first material to provide structural strength coated with one or more additional materials to provide biocompatibility and/or biodurability. Although illustrated as a planar element, this is not a requirement; the moving member 210 may be curved or comprise multiple conjoined non-coplanar elements, preferably to generally match the curvature of the location of the eye where it will be implanted. The moving member 210 may also be fabricated to include various structures or protuberances on any of its surfaces designed to maximize and/or localize mechanical stimulation/irritation.

In this embodiment, an actuator 212 comprises at least one projecting arm coupled to (e.g., integrally formed with) the moving member 210. The actuator 212 may be fabricated from the same or different materials as the moving member 210, with the additional design constraint that the actuator 212 is intended to directly contact the fluid material in the vitreous cavity. Although a single actuator 212 is illustrated in FIG. 9, more than one such actuator could be employed, and the actuator(s) can be positioned differently relative to the moving member 210 (e.g., at the ends rather than at or near the middle). Furthermore, the actuator(s) need not project perpendicularly from the moving member 210, as shown, but may project at any convenient angle. Further still, the actuator(s) need not be formed as substantially planar structures, as shown, but may incorporate various divergent, convergent and/or curving surfaces or vanes as a matter of design choice. All edges of the device can be rounded or otherwise smoothed out to minimize the likelihood of catching and tearing of delicate ocular tissues.

Figure 10:
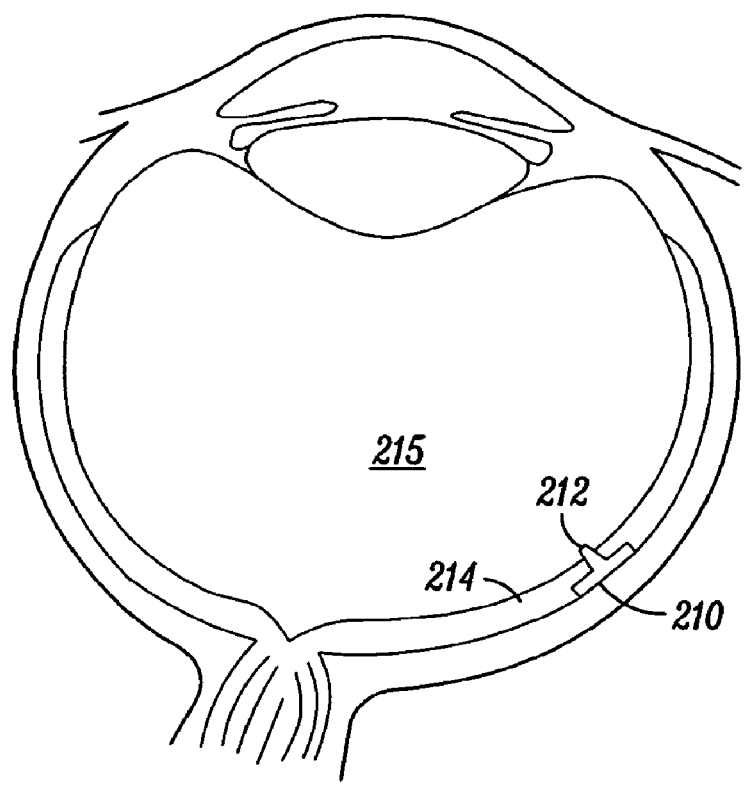
FIG. 10 is a top-cross section of an eye illustrating post-implantation placement of the device of FIG. 9.
Figure 11:
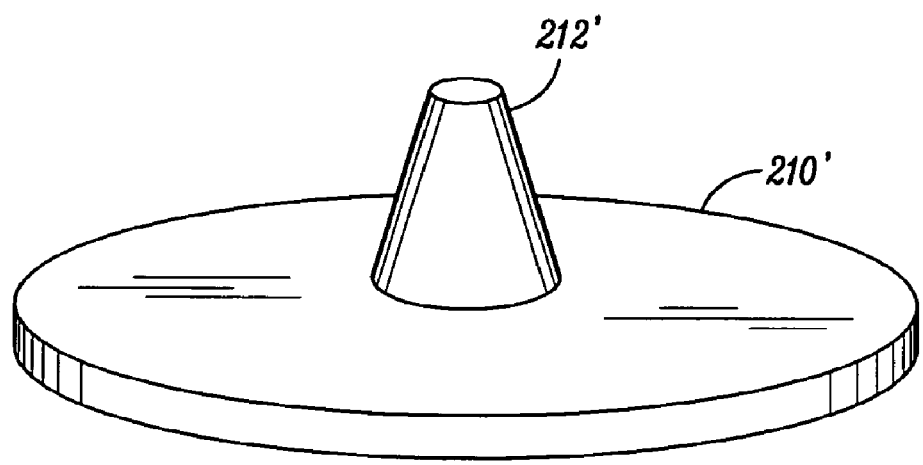
FIG. 11 is a perspective view of an alternative embodiment of the first exemplary device of FIG. 9.

As mentioned above, the actuator 212 is intended to contact the fluid material (e.g., comprising the vitreous or a replacement material) within the vitreous cavity directly. The vitreous comprises a clear, gel-like, relatively viscous material and, as a result, presents an inertial differential at the surface of the retina. Note that a replacement material within the vitreous cavity such as saline or aqueous, although less viscous, would still impart an inertial differential at the retinal surface. That is, as the eye moves by rotating within the orbit, differences in movement of the fluid material within the vitreous cavity relative to the surface of the retina are induced. As illustrated in FIG. 10, the actuator 212 exploits these differences by extending through the retina 214 into the fluid material within the vitreous cavity 215. As the eye moves, movement of the fluid material induces movement in the actuator 212 and, consequently, the moving member 210. Through selection of appropriate dimensions of the actuator 212 and moving member 210, and/or the rigidity of the connection between the actuator and the moving member 210, a controlled amount of movement may be induced in the moving member 210 to achieve a therapeutically-effective level of stimulation/irritation. As illustrated, the actuator 212 will be more susceptible to forces applied parallel to the longitudinal axis of the device, as opposed to at an angle relative to the longitudinal axis. An alternative embodiment is illustrated in FIG. 11 which is designed to be equally susceptible to forces applied to the actuator 212', regardless of their direction. Although not illustrated in FIG. 11, vanes or fins radially (or otherwise) extending from the actuator 212' could be employed to further harness the forces present at the retinal surface. Likewise, in this embodiment, the moving member 210' is circular to provide maximum stimulation to surrounding tissues regardless of the direction of the forces present at the actuator 212'. Note that, although a single device is shown in FIG. 10, it is understood that multiple such devices could be implanted within an eye.

Figure 12:
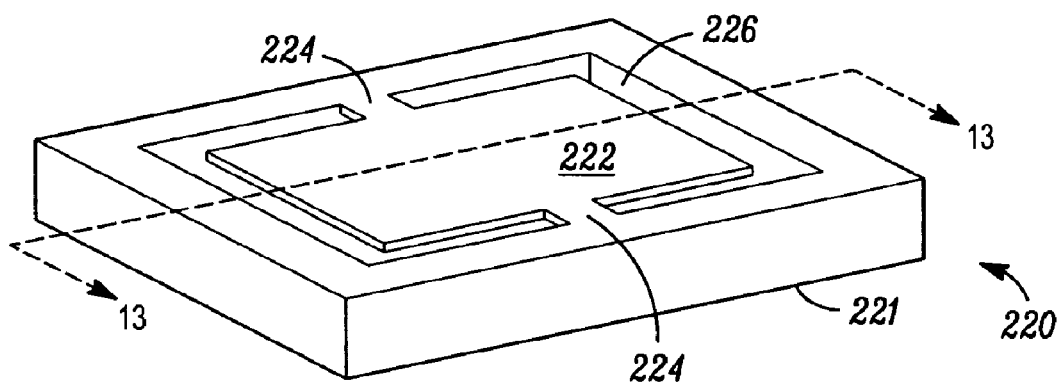
FIG. 12 is a perspective view of a second exemplary device in accordance with the schema of FIG. 8.
Figure 13:
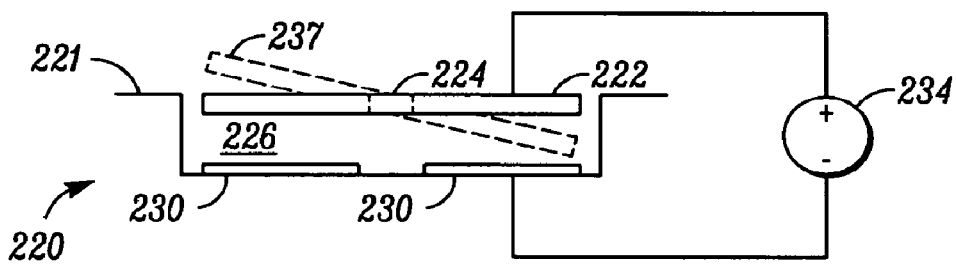
FIG. 13 is a cross-section along line 12-12' of FIG. 12 and further illustrating operation of the second device.

Referring now to FIGS. 12 and 13, a second exemplary device 220 in accordance with the schema of FIG. 8 is illustrated. In particular, the device 220 of FIGS. 12 and 13 is representative of a family of devices in which a body member is provided to support the moving member. In this example, the body member 221 comprises a relatively low-profile base supporting the moving member 222 through integrally-formed supports 224. Together, the moving member 222 and supports 224 form a torsional resonator-like structure sometimes found in the art of micro-electromechanical systems (MEMS). As know in the art of MEMS, such a device can be fabricated from silicon using well-known processing techniques, although other materials may be equally employed. Silicon construction is particularly advantageous because it provides to the opportunity to incorporate electrical elements.

The moving member 222 is positioned over a cavity 226 formed within the body member 221. Within the cavity, one or more electrodes 230 are formed. Although not shown in FIGS. 12 and 13, corresponding electrodes are deposited on or integrally formed with the moving member 222 substantially in alignment with the electrode(s) 230 residing within the cavity 226. As known in the art, application of a voltage 234 across the cavity electrodes 230 and the moving member 222 electrodes will give rise to electrostatic attractive and/or repulsive forces. For example, in FIG. 13, application of a voltage from the voltage source 234 as shown induces attractive forces between the moving member 222 and the cavity electrode 230, thereby causing the moving member 222 to rotate about an axis defined by the supports 224. Note that, in this embodiment, the actuator encompasses the voltage source and electrodes giving rise to the electrostatic force. Such rotation (illustrated by the dashed lines) consequently causes a leading edge 237 of the moving member 222 to impinge upon adjacent tissue, thereby stimulating/irritating such tissue. In practice, to prevent the dissipation of electrical charges through the conductive media presented by ocular tissues, at least all charge-carrying portions of the device 220 are electrically insulated. Such electrical insulation can be provided by a biodurable/biocompatible coating, such as but not limited to parylene or other materials as known in the art, applied to substantially all surfaces of the device 220.

The voltage source 234, although represented in the abstract in FIG. 13, could take any of a number of forms. For example, in a presently-preferred embodiment, photovoltaic elements such as photodiodes can be incorporated into the device 220 (particularly where the body member 221 is fabricated from silicon) and electrically coupled to the electrodes using well known techniques. Entire arrays of moving members could be created along side corresponding photovoltaic elements that supply the necessary electrical charges to one or more neighboring devices. Alternatively, more than one device 220 could be powered by a larger, shared photovoltaic device or devices. Regardless, in this manner, ambient (or artificially provided) light can be used to derive the electrical charges used to induce movement in the device(s). Alternatively, one or more extraocular electrical sources could be employed, although such an approach is less preferred given the likely need for implanted wires or less efficient wireless power transmission.

Figure 14:
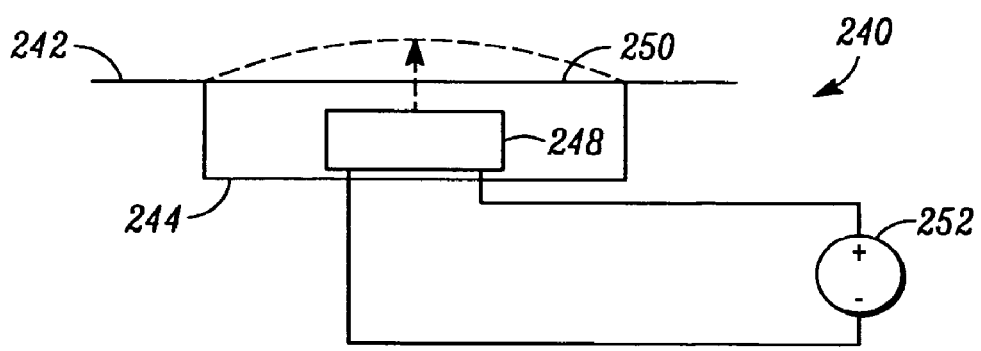
FIG. 14 is a cross-section of a third exemplary device in accordance with the schema of FIG. 8.

Referring now to FIG. 14, a third exemplary device 240 in accordance with the schema of FIG. 8 is illustrated. A cavity 244 is formed in a body member 242, preferably but not necessarily formed of silicon, and sealed off with a deflectable, biocompatible/biodurable membrane 250. In this instance, the membrane 250 serves as the moving member. The membrane 250, which may hermetically seal the cavity 244 and may be fabricated from silicone, PMMA, parylene, latex, diamond-like carbon or other materials offering good biocompatibility and flexibility. Note that, although a single cavity and membrane are illustrated in FIG. 14, multiple cavities and/or multiple membranes may be equally employed. An actuator 248, provided within the cavity 244, is schematically illustrated in FIG. 14. The actuator 248 operates to impart a force (illustrated by the dashed arrow) on the membrane 250 such that the membrane is displaced, thereby coming into contact with, and likewise displacing, adjacent ocular tissues. Preferably, the actuator 248 is coupled to a voltage source 252 that provides power such that the actuator can impart force on the membrane 250. As in the embodiment of FIGS. 12 and 13, the voltage source 252 preferably comprises one or more photovoltaic devices, preferably integrally formed in the body member 242, although other voltage sources may be equally employed. Additionally, an array of such membrane-based devices could be formed within the body member 242. Regardless, various devices or combination of devices can be employed to implement the actuator 248, several of which are discussed below.

For example, in one embodiment, a fluid (preferably having a relatively low boiling point and exhibiting good biocompatibility) is placed in (and, preferably, completely fills) the cavity 244. Additionally, a heating element is also placed within the cavity while retaining a hermetic seal around the cavity. The heating element is further coupled to the voltage source 252. Collectively, the voltage source 252, heating element, cavity 244 and fluid function as the actuator. When power is applied to the heating element, the resulting heat causes the fluid to expand, leading to a pressure increase within the cavity 244. The increase in pressure causes the membrane 250 to deflect (illustrated in dashed lines) and thereby impinge upon adjacent ocular tissues. When heat is removed, the fluid cools and condenses, pressure decreases within the cavity, and the membrane returns to its relaxed state.

In another embodiment, the cavity 244 is provided with one or more bleed or flow orifices (for example, formed in the floor of the cavity 244) such that, after implantation of the device 240, tissue fluids slowly ingress into the cavity 244. At least two electrodes are fabricated into the cavity floor and connected to the voltage source 252. In this instance, the voltage source 252, electrodes, cavity 244 and tissue fluids collectively function as the actuator. When a voltage is applied at the electrodes, electrolysis creates gas bubbles at the electrodes. The size of the gas bubbles is proportional to the applied power. Regardless, the increased volume of the gas bubbles within the cavity 244 causes the membrane 250 to deflect. Thereafter, at the end of each stimulation cycle, the cavity is allowed to slowly equilibrate, via the flow orifices, with the tissue fluids and membrane 250 returns to its original position.

In yet another embodiment, the actuator 248 may comprise a fulcrum and lever arrangement, disposed within the cavity 244, in which one end of the lever is coupled to a shape-altering material. For example, so-called electro-active polymers (EAPs) or "artificial muscles" which alter their shape in response to an applied voltage may be employed for this purpose. U.S. Pat. No. 6,511,508 and U.S. Patent Application No. 20030139808 describe the use of a variety of EAP as well as other artificial muscle materials that may be used in conjunction with the present invention, the teachings of which are incorporated herein by this reference. In this case, one end of a length of EAP is affixed within the cavity 244 while the other end of the length of EAP is coupled to one end of the lever. Additionally, the EAP is coupled to the voltage source 252. Collectively, the fulcrum, lever, EAP and voltage source 252 function as the actuator in this instance. As known in the art, when a voltage is applied to a properly configured EAP, movement can be induced in the EAP. Using well-known mechanical principals, such movement by the EAP causes the lever to rotate about the fulcrum. In turn, the rotation of the lever causes the membrane 250 to deflect, thereby displacing adjacent ocular tissues. When the EAP is thereafter allowed to relax or is otherwise returned to its original state, the lever and membrane 250 return to their original positions.

In addition to the embodiments described in FIGS. 9-14, other technologies could be employed when implementing devices in accordance with the schema of FIG. 8. For example, piezoelectric materials, i.e., materials that alter their shape in response to an applied voltage, are well known in the art. Using such materials, a moving member can be fashioned directly out of a piezoelectric material such that the voltage source functions as the actuator, or a non-piezoelectric material could be used to fashion a moving member that in turn is mechanically coupled to a piezoelectric actuator. Alternatively, the EAPs described above, rather than being used to induce movement in another structural element, could be directly fashioned into a moving member such that motion induced in the EAP is directly transferred to, for example, a deflectable membrane without the aid of an intervening device. Regardless, biocompatible materials are preferred.

Figure 15:
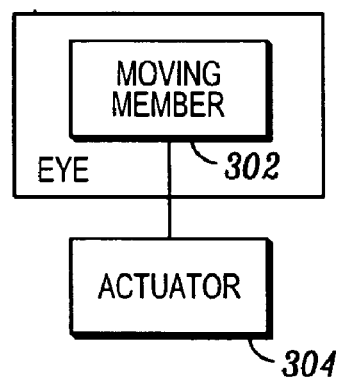
FIG. 15 is a schematic illustration of a mechanically activated object in accordance with another embodiment of the present invention.

A second schema of mechanically activated embodiments is illustrated in FIG. 15 wherein at least one moving member 302, implanted on or within the eye, is acted upon by an extraocular actuator 304. As in the first schema, the moving member 302 is configured to contact at least a portion of the eye, including any of the various structures of the eye, preferably a retina of the eye. Furthermore, although preferably configured for implantation in the subretinal space, the moving member 302 may be equally configured for implantation in virtually any location of the eye, e.g., epiretinally, subsclerally/suprachoroidally, sclerally, subchoroidally, on the conjunctiva, etc. Regardless of its location when implanted, the moving member, when acted upon by the actuator 304, displaces the tissues of the eye with which it is in contact thereby stimulating the eye.

In the second schema, unlike the first, the actuator 304 is extraocular (which is not necessarily exclusive of being implanted within the body, e.g., intraorbitally) but nevertheless acts upon the moving member 302. Examples of actuators suitable for this purpose include oscillators that induce mechanical waves in the ocular tissues and magnetic fields that penetrate the ocular tissues. Further examples include actuators that are mechanically and/or electrically coupled through an appropriate linkage to the moving member, which linkage penetrates the intervening ocular tissues.

Figure 16:
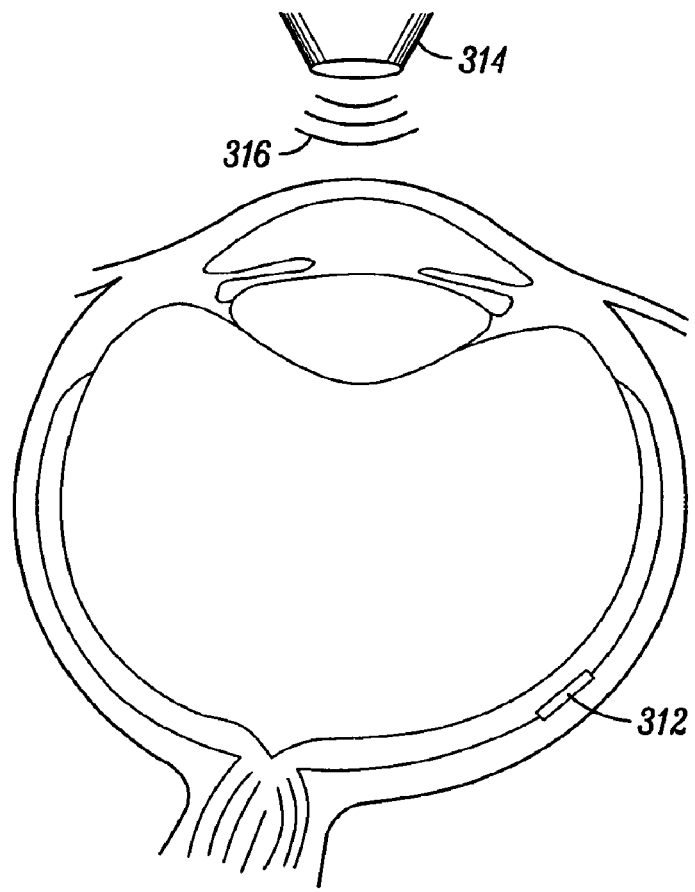
FIG. 16 is a top cross-section of an eye illustrating a class of exemplary devices in accordance with the schema of FIG. 15.

FIG. 16 illustrates a system in accordance with the schema of FIG. 15 in which an implanted moving member 312 is acted upon by an extraocular actuator 314. In one embodiment, the moving member 312 comprises an object or device having a natural vibration frequency. When provided with an appropriate vibratory stimulus, the object will likewise vibrate at its natural vibration frequency. A vibratory stimulus that is most closely tuned to a natural frequency of an object will induce the greatest magnitude vibrations in the object. As such, the nature of the vibratory stimulus can be controlled to likewise control the magnitude of the induced vibrations. The particular resonant frequencies of a given object (not accounting for environmental or other damping effects) will depend on the physical characteristics of the object, e.g., its mass, shape, dimensions, etc.

In accordance with such a system, the moving member 312 can be designed to have a specific natural frequency. Being implanted, the moving member 312 is preferably fabricated from and/or coated with suitably biocompatible/biodurable materials. The actuator 314, in this case a mechanical oscillator, generates mechanical waves 316 (substantially at the natural frequency of the moving member, optimally) that propagate through the ocular media and impinge upon the moving member 312. Depending on how close the impinging waves 316 are to the natural frequency of the moving member 312, and taking into account the damping effects of the surrounding tissues, vibrations of controlled (but variable) magnitudes are imparted by the moving member 312 upon the surrounding ocular tissues (e.g., the retina) thereby stimulating/irritating the tissues. Techniques for generating mechanical waves, and hence for implementing an actuator 314 capable of generating such mechanical waves, are well known in the art and need not be described in further detail here. In practice, such an oscillator can be mechanically coupled directly to a surface of the eyeball through an appropriate (e.g., fluid) interface, or indirectly through tissues or structures adjacent the eyeball (e.g., through the eyelids or bones of the orbit). Although an external actuator 314 is depicted in FIG. 16, it is understood that the actuator 314 could be implanted within the body and yet remain extraocular. For example, through the use of appropriate electrical connections, such an actuator could be implanted within the orbit of an eye.

In another embodiment of the schema of FIG. 15, the moving member 312 comprises a magnet. Movement of a magnet may be induced by changes (relative to the magnet) in a magnetic field in which the magnet resides. Thus, movement of the magnet itself through a static magnetic field will induce further movement of the magnet and/or the magnetic field itself can be varied. Thus, for example, the moving member 312 may comprise a suitably-dimensioned magnet that is either fashioned from biocompatible/biodurable materials or that is rendered biocompatible/biodurable through suitable coatings such as, but limited to, parylene. In this case, the actuator 314 may comprise a source of a time-varying magnetic field 316, such as an electromagnet. When the time-varying magnetic field 316 impinges upon the magnet, it induces movement in the magnet 312 commensurate with the rate of variance of the magnetic field. By adjusting the strength and rate of variance of the magnetic field, the movement of the magnet 312 may likewise be controlled. As an alternative, a static, time-invariant magnetic field may be employed such that movement of the magnet through the static magnetic field induces vibrations in the dipole. For example, a sufficiently powerful magnetic field could be established extraocularly (e.g., through extraocular implantation of permanent magnets or placement of sufficiently powerful magnets outside the head). Given the natural movement of the eye, the implanted magnet 312 will move through the static magnetic field, thereby inducing further movement of the magnet.

The present invention provides mechanically activated objects or devices for use in treating degenerative retinal diseases. In keeping with the hypothesis that mechanical stimulation or irritation of various tissues of the eye may give rise to upregulation of endogenous beneficial survival-type factors, the present invention teaches various mechanically activated approaches for eliciting such stimulus. In this manner, it may be possible to treat degenerative retinal diseases for which there were no previous treatments or cure.

Although particular embodiments have been disclosed herein in detail, this has been done for purposes of illustration only and is not intended to be limiting with respect to the scope of the appended claims that follow. In particular, it is contemplated by the inventors that various substitutions, alterations, and modifications may be made to the invention without departing from the spirit and scope of the invention as defined by the claims. Other aspects, advantages, and modifications are considered to be within the scope of the following claims.

We claim:

1. A device for treatment of degenerative retinal disease, comprising:
   a moving member configured for chronic contact with at least a portion of an eye; and
   an actuator for activating the moving member to stimulate the eye to effectuate treatment of the degenerative retinal disease,
   wherein the moving member comprises a magnet and the actuator comprises a magnetic field source.

2. The device of claim 1, wherein the actuator is distally located relative to the moving member.

3. The device of claim 1, wherein the moving member is configured for contact with a retina of the eye.

4. The device of claim 3, wherein the moving member is configured for implantation in a subretinal space of the eye.

5. The device of claim 1, wherein the actuator comprises a projecting arm coupled to the moving member.

6. The device of claim 1, wherein the magnetic field source comprises an extraocular magnetic field source.

7. The device of claim 1, wherein the magnetic field source comprises a time-varying magnetic field source.

8. A device for treatment of degenerative retinal disease, comprising:
   a moving member configured for chronic contact with at least a portion of an eye; and
   an actuator for activating the moving member to stimulate the eye to effectuate treatment of the degenerative retinal disease,
   wherein the moving member comprises a body having a natural vibration frequency and the actuator comprises an oscillator operating substantially at the natural vibration frequency.

9. The device of claim 8, wherein the oscillator comprises an extraocular oscillator.

10. A device for treatment of degenerative retinal disease, comprising:
    a moving member configured for chronic contact with at least a portion of an eye;
    an actuator for activating the moving member to stimulate the eye to effectuate treatment of the degenerative retinal disease; and
    a body member supporting the moving member;
    wherein the body member supports the actuator, and wherein the actuator comprises an electrical source.

11. The device of claim 10, wherein the moving member comprises an electrostatically-activated member.

12. The device of claim 10, wherein the moving member comprises a piezoelectric member.

13. The device of claim 10, wherein the moving member comprises an electroactive polymer member.

14. The device of claim 10, wherein the actuator comprises a heating element coupled to the electrical source.

15. The device of claim 14, wherein the moving member comprises a deflectable membrane sealing a cavity formed in the body member, the cavity comprising a fluid, and wherein the heating element is positioned to heat the fluid thereby causing expansion of the membrane.

16. The device of claim 14, wherein the moving member comprises a shape memory alloy in thermal communication with the heating element.

17. The device of claim 10, wherein the electrical source comprises a photovoltaic element.

* * * * *